(12) United States Patent
Son

(10) Patent No.: US 11,076,975 B2
(45) Date of Patent: Aug. 3, 2021

(54) CARPAL TUNNEL SYNDROME RELIEF DEVICES AND METHODS OF USING THEREOF

(71) Applicant: Jae S. Son, Rolling Hills Estates, CA (US)

(72) Inventor: Jae S. Son, Rolling Hills Estates, CA (US)

(73) Assignee: Sohn Inc., Hawthorne, CA (US)

( * ) Notice: Subject to any disclaimer, the term of this patent is extended or adjusted under 35 U.S.C. 154(b) by 273 days.

(21) Appl. No.: 16/139,050

(22) Filed: Sep. 23, 2018

(65) Prior Publication Data

US 2020/0093627 A1    Mar. 26, 2020

(51) Int. Cl.
*A61F 5/01* (2006.01)

(52) U.S. Cl.
CPC .................................. *A61F 5/0118* (2013.01)

(58) Field of Classification Search
CPC ...... A61F 5/0118; A61F 5/013; A61F 5/0111; A61F 5/05866; A61F 5/30; A61F 5/32; A61F 13/00021; A61F 2013/00272; A61F 2013/0028; A61F 1/10; A61F 1/107; A61F 2013/00374; A61F 2013/00382; A61F 2013/00451
See application file for complete search history.

(56) References Cited

U.S. PATENT DOCUMENTS

| | | | |
|---|---|---|---|
| 4,047,250 A | 9/1977 | Norman |
| 4,048,991 A | 9/1977 | Marx |
| 4,628,918 A | 12/1986 | Johnson |
| 4,883,073 A | 11/1989 | Aziz |
| 4,966,137 A | 10/1990 | Daviny |
| 5,256,136 A | 10/1993 | Sucher |
| 5,267,943 A | 12/1993 | Dancyger |
| 5,372,575 A | 12/1994 | Sebastian |
| 5,468,220 A | 11/1995 | Sucher |
| 5,921,949 A | 7/1999 | Dray |
| 6,217,536 B1 | 4/2001 | Gustafson |
| 6,238,411 B1 | 5/2001 | Thorner |
| 6,244,265 B1 | 6/2001 | Cronk |
| 6,315,748 B1 | 11/2001 | Morgan |
| 6,375,667 B1 | 4/2002 | Ruch |
| 7,793,661 B2 | 9/2010 | Macken |
| 8,047,201 B2 | 11/2011 | Guyuron |
| 2008/0257341 A1 | 11/2008 | Ierulli |
| 2010/0121241 A1 | 5/2010 | Nyi |
| 2011/0152921 A1 | 6/2011 | Lehman |

(Continued)

*Primary Examiner* — Rachael E Bredefeld
*Assistant Examiner* — William T Kao
(74) *Attorney, Agent, or Firm* — Boris Leschinsky

(57) ABSTRACT

A set of carpal tunnel syndrome relief devices is provided for treatment of a subject. The set includes several devices configured to be applied to a wrist which may have various shapes and sizes. Each device may be configured for an adhesive application to a skin area on a proximal side of a wrist over a median nerve of the subject. One device may be selected to match the profile of the skin of the subject and provide a distance from the peak of the middle portion to the underlying skin of about 3 to 6 mm—so as to achieve optimal pull of the skin above the median nerve and relief of carpal tunnel syndrome. An alternative, subject-specific design of the carpal tunnel syndrome relief device profile is also described.

7 Claims, 10 Drawing Sheets

(56) References Cited

U.S. PATENT DOCUMENTS

| | | | |
|---|---|---|---|
| 2011/0166594 A1 | 7/2011 | Eull | |
| 2013/0218060 A1* | 8/2013 | Bushby | A61F 5/0118 602/21 |
| 2014/0114219 A1 | 4/2014 | Nazari | |
| 2014/0236059 A1 | 8/2014 | Son | |
| 2015/0297301 A1 | 10/2015 | Nazari | |
| 2016/0296406 A1* | 10/2016 | Heyl | A61H 1/02 |
| 2017/0156812 A1* | 6/2017 | Nazari | A61F 13/10 |
| 2019/0388263 A1* | 12/2019 | Emslander | A61L 15/125 |

* cited by examiner

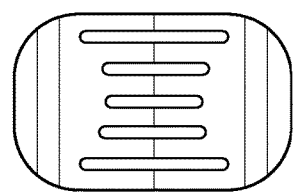 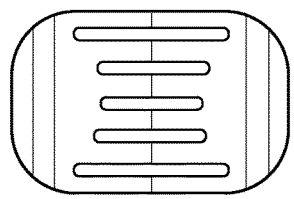 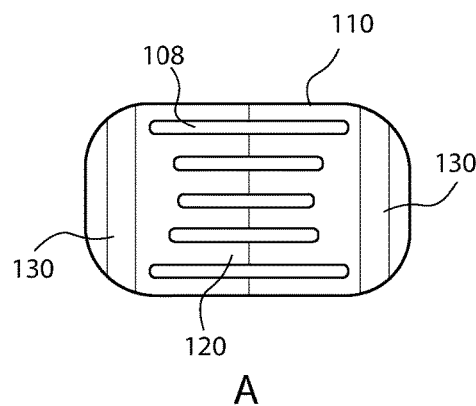
A  A  A
  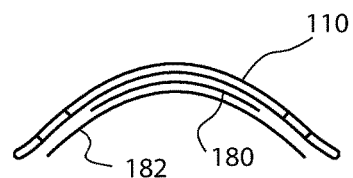
B  B  B
Fig. 6  Fig. 7  Fig. 8

Round - Ratio 3.9

Average - Ratio 5.3

Flat - Ratio 6.2

CARPAL TUNNEL SYNDROME RELIEF DEVICES AND METHODS OF USING THEREOF

BACKGROUND

The present invention relates generally to external devices for relief of compressed tissue. More particularly, the invention describes a resilient strip configured to rearrange soft tissue in the area of a human wrist so as to relief median nerve compression, a condition generally known as a carpal tunnel syndrome.

"Carpal tunnel syndrome", as well as many cases of tendinitis and other cumulative trauma disorders (CTD's) of the wrist and forearm (which are all commonly referred to as Carpal Tunnel Syndrome in this application), result from repeated abrasion of the tendons and the median nerve that pass through the carpal tunnel. Excessive pressure on the carpal tunnel tissues causes pain and tingling sensation along the pathway of the median nerve, which are the classic symptoms of this condition. Other typical symptoms are numbness and tingling in the thumb, index finger, middle finger, and radial half of the ring finger. Additional common manifestations of this condition include burning dysesthetic wrist pain, as well as loss of grip strength and dexterity. Symptoms are often worse at night and can be exacerbated by forceful activity and extreme wrist positions.

Carpal tunnel syndrome affects approximately 3 percent of adults in the United States. It is the most commonly diagnosed entrapment neuropathy. Carpal tunnel syndrome is a frequent complication of pregnancy, with a prevalence reported as high as 62%. Median nerve function is impaired in virtually all pregnant women during the third trimester, even in the absence of symptoms. In one study, 30% of frequent computer users complained of hand paresthesias, 10% met clinical criteria, and 3.5% had abnormal nerve conduction. In another study, the overall self-reported prevalence of tingling/numbness in the right hand at baseline was 10.9% for computer users and interview follow up confirmed that prevalence of tingling/numbness due to the median nerve was 4.8%.

Current mainstream non-surgical treatments of carpal tunnel syndrome include rest, restriction from traumatizing activities, splinting the wrist in a neutral position, anti-inflammatory medication, and cortisone injections.

While many clinical studies are published on non-surgical treatments of carpal tunnel syndrome, their conclusions vary between the researchers. One summary paper of 20 randomized clinical studies showed strong and moderate evidence for the effectiveness of oral steroids, steroid injections, ultrasound, electromagnetic field therapy, nocturnal splinting, use of ergonomic keyboards compared with a standard keyboard, and traditional cupping versus heat pads in the short term. However, there is limited evidence to indicate that splinting, acupuncture, yoga, and therapeutic ultrasound may be effective in the short to medium term of up to 6 months. Another study found moderate supporting evidence for ultrasound in the midterm. Despite limited efficacy, these conservative treatments have a negligible incidence of serious complications and should be used more widely until surgical procedures can be improved to have comparable safety profile.

Some form of wrist support or a splint is normally used in the early stages of treatment. These devices are used in an attempt to delay progression of the condition or as an adjunct to some other treatment in an effort to lessen the pain and aid in the return to normal function that are clearly of benefit are neutral-angle wrist splinting, with a reported success rate of 37%. Subsequent to surgery, wrist splints are frequently used to support the wrist and aid in recovery.

There is strong evidence that local corticosteroid injections give short-term relief (two to four weeks), for carpal tunnel syndrome patients. Steroids are reported to provide initial relief in up to 70% of patients but frequent relapses are common. Moreover, although higher doses of steroid injections seem to be more effective in the midterm, the benefits of steroids injections are not maintained in the long term.

Open carpal tunnel release is the most commonly performed surgical procedure for this condition. Open surgery involves an incision on the palm about an inch or two in length. Through this incision, the skin and subcutaneous tissue is divided, followed by the palmar carpal fascia, and ultimately the transverse carpal ligament to allow more room for the contents of the carpal tunnel, i.e., an increase in the diameter-to-contents ratio.

Splints and supports are often the earliest form of treatment and prevention because it is inexpensive and simple to use. If the efficacy of these devices could be improved, the benefit to the patient and the economy would be significant. However, the cause of carpal tunnel such as over working, lack of exercise or stretching, poor ergonomic setup all needs to be addressed to obtain long term relief.

Prior art describes many splints and various supporting devices designed for treating the symptoms of the carpal tunnel syndrome. Below described patents are incorporated herein in their respective entireties.

Some examples of wrist braces and supporting devices may be found in U.S. Design Pat. No. 339,866 and U.S. Pat. No. 4,883,073. Such supports typically include metal or some type of reinforcing part to restrict or limit wrist or hand movement. Other examples are shown in U.S. Pat. Nos. 4,047,250, 4,883,073 and 5,267,943. These devices typically include a part that fits around the thumb and hand such as a thumb loop, or some other means of securing the device to the arm and hand to prevent slippage. Devices like those referenced above, either partially or totally limit or inhibit flexion and/or extension movements of the wrist while also restricting abduction and adduction movements. Dexterity of the hand, wrist and fingers is generally compromised.

U.S. Pat. No. 4,048,991 shows a device with a circumferential rigid member that compresses the wrist in a so-called neutral position. U.S. Pat. Nos. 4,628,918 and 5,921,949 describe a corrective support designed specifically for the treatment of a carpal tunnel syndrome by wrapping a wrist strap with a Velcro fastening mechanism with an inflatable bladder mounted in the wrist strap that squeezes the sides of the wrist.

U.S. Pat. No. 4,966,137 utilizes a metal diamond structure to compress and squeeze the sides of the distal forearm, i.e. the radius and ulna in an attempt to alter the carpal tunnel. U.S. Pat. No. 5,372,575 represents yet another type of support, which is intended to compress musculoskeletal structures and achieve a therapeutic effect via removable bladder and foam padding underneath a Velcro strap. U.S. Pat. Nos. 5,468,220 and 5,256,136 attempt to stretch the flexor retinaculum using a metal bracelet with adjustable springs and compression plates.

U.S. Pat. No. 6,244,265 is related to the present invention in that it is attached to a skin via an adhesive layer. This device is a nasal dilator that includes an elongated substrate, with or without a dilating component or portion, having top and bottom surfaces and a pressure-sensitive adhesive disposed on the bottom surface.

U.S. Pat. No. 6,315,748 is an orthopedic device for the treatment of physical disorders characterized by region (s) of localized, undue compression of body tissue leading to nerve compression and/or damage, such as carpal tunnel syndrome. This invention includes a central, resilient, stretchable tensioning segment placed on the back of a subject's hand, whereupon three straps are pulled and adhered to the subject's palm in a fashion to flatten the palm by applying continuous tensile forces through the straps which is supposed to reduce the median nerve compression and alleviate symptoms.

U.S. Patent Application 2014/0236059 by the present inventor describes a carpal tunnel syndrome relief device comprising a curved resilient strip with a pressure sensitive adhesive on the inside thereof. Deformation of the strip prior to use causes central tissue above the median nerve to be lifted while compressing tissue nearby the median nerve. This application is incorporated herein by reference in its entirety.

The above referenced devices fail to account for the differences in sizes and shapes of a human wrist. Generally speaking, most of these devices are configured for application on the palm of the hand, which may not be the most effective and convenient location for applying carpal tunnel syndrome relief therapy. In addition, these devices are usually offered in a single size and a fixed geometry configuration. This creates a condition when for smaller wrists the device may be too aggressive in its action while for larger wrists the device is not sufficiently effective. Even if multiple device sizes are provided, they typically follow the Small-Medium-Large convention where the shape of the device is generally the same between different sizes, but the actual dimensions are scaled up and down to accommodate subjects of different height and weight.

While this approach of scaling the size of the device may be suitable for many other medical devices, in case of a carpal tunnel syndrome, a subject-specific and well-defined lifting of the skin and underlying tissue is required to achieve a positive outcome. Prior art devices simply do not provide a flexibility to choose the device most suitable for an individual subject.

Therefore, a need exists for a simple to use and inexpensive device capable of providing lasting relief for carpal tunnel syndrome. Ideally, such device should be non-invasive, inexpensive, and suitable for self-application by the subject in a broad range of anatomical shapes and sizes of a human wrist.

SUMMARY

Accordingly, it is an object of the present invention to overcome these and other drawbacks of the prior art by providing non-invasive carpal tunnel syndrome relief devices and methods of use aimed to relieve compression of the median nerve and surrounding tissues.

It is a further object of the present invention to provide a set of carpal tunnel syndrome relief devices and methods of using thereof to cover a broad range of possible anatomical shapes and sizes for various subjects so as to assure optimum reshaping of tissues surrounding the median nerve for each subject.

It is a further yet object of the present invention to provide devices and methods to improve circulation in the tissues surrounding the median nerve of a subject so as to relieve median nerve inflammation.

It is another object of the present invention to provide carpal tunnel syndrome relief devices and methods of their use that are non-invasive and can be self-applied.

It is a further object of the present invention to provide carpal tunnel syndrome relief devices and methods to cause optimal reshaping of the soft tissues of the wrist in a manner that is beneficial for carpal tunnel relief.

It is yet a further object of the present invention to provide carpal tunnel devices and methods to apply continuous suitable tension on the soft tissues of the wrist area so as to provide continuous pressure relief of the median nerve.

The present invention is generally concerned with improved methods and devices for the treatment of physical disorders characterized by a region of localized, undue compression of body tissue, for example a carpal tunnel syndrome, by directly applying negative pressure (pulling tension) to the affected area. In so doing, a suitably selected device of the invention relieves pressure on the median nerve, carpal ligaments and other soft tissue structures of the wrist while allowing full and unrestricted motion of the wrist, hand and fingers. Once the tissue compression is relieved, a normal (or medically-assisted) healing process may take place providing for a longer lasting relief.

Provided is a set of carpal tunnel syndrome relief devices configured to be applied for various shapes and sizes of a human wrist. Positioning of the device over the wrist is preferred to a conventional position over a palm as it is less intrusive in everyday life. At least one predetermined criteria may be used to select the most appropriate device for a particular subject. Each device may be configured for an adhesive application to a skin area on a proximal side of a wrist over a median nerve of the subject.

To do so, each carpal tunnel syndrome relief device of the set may comprise a resilient arch-curved strip of a generally elongated rectangular shape with rounded edges, so as to make it atraumatic when in contact with the skin. Each resilient strip may include a middle portion equipped with or adapted to receive a stand-alone pressure sensitive adhesive layer on a concave side thereof. The rest of the concave area of the resilient strip away from the middle portion constitutes an adhesive-free periphery. A certain curvature of the resilient strip may be provided, as defined on a concave side by a chord with a length of about 20 mm to about 35 mm and a height from a peak of the middle portion to said chord.

Several carpal relief devices may be provided in the set, such as:
   a first carpal tunnel syndrome relief device with a ratio of the chord length to the height of about 3.5 to about 4.5,
   a second carpal tunnel syndrome relief device with the ratio of the chord length to the height of about 4.5 to about 5.5, and
   a third carpal tunnel syndrome relief device with the ratio of the chord length to the height of about 5.5 to about 6.5.

In use, a wrist of the subject may be scanned or non-invasively imaged to determine the shape of the curved profile of a wrist area on a proximal side thereof over a median nerve. One of the carpal relief devices may be selected from a set of such devices that would most closely match at least one predetermined criteria, such as providing an offset of about 5 mm between the concave portion of the device and the underlying skin over the median nerve of the subject. The selected device can then be applied to the skin by exposing the adhesive layer and pressing the device to temporarily reshape thereof and place it in contact with the skin. Release of the device compression afterwards would cause the middle portion of the device to provide a pulling action on the skin above the median nerve while compressing the skin on a periphery of the device.

In embodiments, the wrist of a subject may be first scanned or evaluated in another way to determine its initial curvature profile and size. A custom device may then be provided in which the resilient strip is shaped to match a predetermined profile designed based on the shape of the wrist of the subject and a predetermined offset at the middle portion of the device. One example of such patient-specific profile may be with a curvature of the concave side of the resilient strip having a chord with a length of about 20 mm to about 35 mm and a height from a peak of the middle portion to the underlying skin area of about 5 mm.

At least two versions of the device may be provided in various embodiments of the invention. In a first version of the device, the pressure sensitive adhesive layer is provided as part of the device and is protected from skin exposure by a removable protective masking tape or paper liner. In use, the protective liner is removed first exposing the underlying adhesive layer. The device is then applied to touch the skin while being flattened causing the resilient strip to be in continuous contact with the skin.

A second version of the device does not provide a pre-assembled adhesive layer residing on the concave portion of the resilient strip. In this case, a double-sided adhesive layer is provided as a separate adhesive strip and is protected on both sides by removable protective liners. In use, the adhesive layer is first applied to the skin by removing a first protective liner. Removing a second protective liner thereafter causes a second side of the adhesive layer to be exposed by facing the concave side of the resilient strip. Applying the resilient strip by flattening it and bringing it close and then in contact with the exposed adhesive layer causes the resilient strip to adhere to the skin via a double-sided adhesive layer so as to then provide a pulling action when released.

To facilitate proper selection of the suitable device for relief of the carpal tunnel syndrome, wrist 3D scanning may be conducted using any suitable technologies. In embodiments, to facilitate home use and self-application of the device, a 3D scanner of a mobile phone may be used for that purpose. A corresponding software may be provided for use with the mobile phone scanner to interpret the scanned shape of the inner portion of the wrist of the subject and either custom design the most appropriate shape of the resilient strip or select the closest match from a number of available shapes.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 6 shows a top view (panel A) and a side view (panel B) of a first exemplary carpal tunnel syndrome relief device from a set of devices to treat carpal tunnel syndrome;

FIG. 7 shows a top view (panel A) and a side view (panel B) of a second exemplary carpal tunnel syndrome relief device from a set of devices to treat carpal tunnel syndrome;

FIG. 8 shows a top view (panel A) and a side view (panel B) of a third exemplary carpal tunnel syndrome relief device from a set of devices to treat carpal tunnel syndrome;

DETAILED DESCRIPTION OF THE PREFERRED EMBODIMENTS OF THE INVENTION

Figure 1:
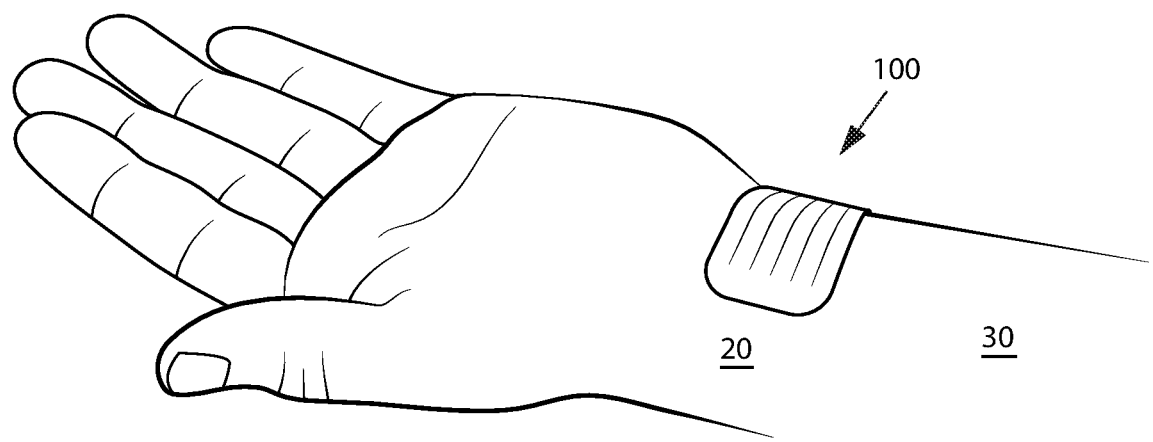
FIG. 1 is a general depiction of a hand with a carpal relief device applied thereto.

The following description sets forth various examples along with specific details to provide a thorough understanding of claimed subject matter. It will be understood by those skilled in the art, however that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

FIG. 1 generally shows the device 100 of the invention placed over a skin area of the inner wrist above the projected location of the median nerve. According to the present invention, lasting carpal tunnel syndrome relief can be achieved by lifting the skin and adjacent tissues away from the median nerve in the volar area 20 on a proximal side of a wrist 30 over the median nerve of the subject.

According to the present invention, the preferred location of lifting the skin may be the inner wrist of the subject, in particular its volar area on a proximal side thereof. More particularly, there may be an optimum extent (distance) of skin lifting. Too little lifting may not be effective to relieve the carpal tunnel syndrome, while too much lifting may cause a corresponding excessive skin deformation and compression in the areas of tissue adjacent to the lifted skin.

To achieve a proper extent of skin lifting, the device 100 may generally comprise a resilient curved strip of an elongated rectangular shape with rounded edges, so as to make it atraumatic when in contact with the skin. The inside surface of the resilient strip may be configured for adhesive attachment to the skin of the subject. After initially deforming to a lesser curved shape causing the device to be flattened, the middle portion of the resilient strip may be adhesively attached to the skin. When released, the middle portion's curvature seeks to return to its original more curved shape and in doing so causes lifting of the skin adhered to the middle portion while simultaneously compressing the skin on both peripheral sides of the resilient, which may be made adhesive-free.

In embodiments, the optimal extent of skin lifting may be achieved by selecting a proper shape of the device 100 and selecting a proper combination of stiffness and resiliency so as to accomplish a continuous pull with a spring-like action of the device when in use. A proper match to the skin curvature of the subject to the curvature of the device is critical in achieving a suitable skin lifting in the optimal range of pull forces.

Figure 2A:
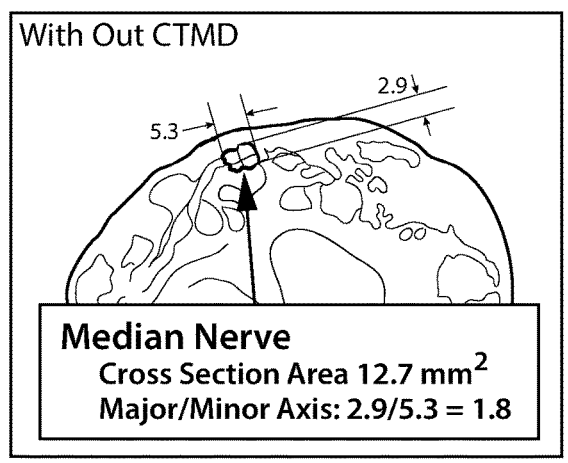
FIGS. 2A and 2B show an MRI-obtained cross-section of a human wrist with pinched median nerve without and with the device of the present invention.
Figure 2B:
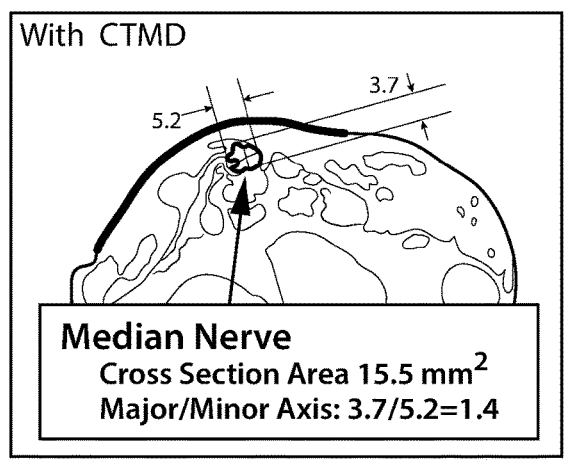

To determine the proper curvature of the device, a detailed understanding of the curvature of the wrist is needed. To evaluate wrist curvatures, a comprehensive MRI study of thirty human subjects was conducted. A comparison of the initial skin profile and position of various wrist tissues in a cross-section of a proximal portion of a wrist was made with and without the use of the skin lifting device. An exemplary cross-section of a human wrist showing the position of the median nerve and surrounding tissues is seen in FIGS. 2A (no device) and 2B (device in use). A significant increase in the cross-sectional area of the median nerve is seen in FIG. 2B in comparison with FIG. 2A as the device decompresses the nerve and makes it more circular by reducing tissue pressure thereon.

Out of thirty adult subjects who were enrolled in the MRI wrist study, three were diagnosed with carpal tunnel syndrome. Subjects were assigned to either a small, medium, or large skin lifting device and the gap between the device and wrist was measured. Contact pressure between the patient and device was also measured using a conformable tactile pressure array sensor attached to the concave side of the device. Basic demographics, medical history, wrist measurements, and a comfort & use survey were taken for each patient.

A broad body mass index (BMI) range was achieved with the subjects that were enrolled, ranging from underweight to just above obese (average BMI 29±6, range 18-40). Negative contact pressures across the center of the device averaged −7.3 mmHg. The locations of acute peak pressures were at the corners of the device, especially the proximo-radial corner. Subjects overall reported the device to be very comfortable and none reported that it was painful. The adhesive layer was firmly attached to the skin for every subject and the device was easy to wear and remove.

Figure 3:
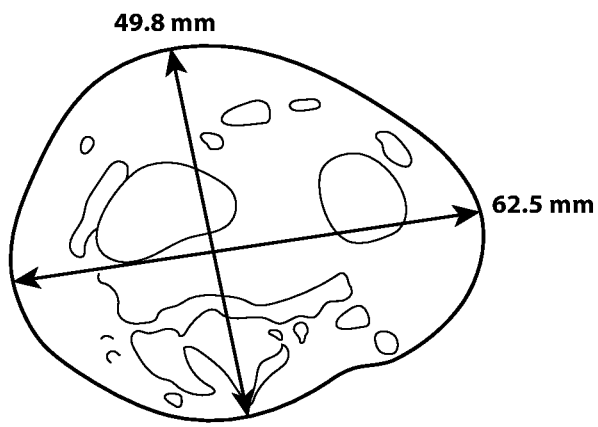
FIG. 3 shows exemplary dimensions obtained during the investigation of sizes and shapes of a human wrist.
Figure 4:
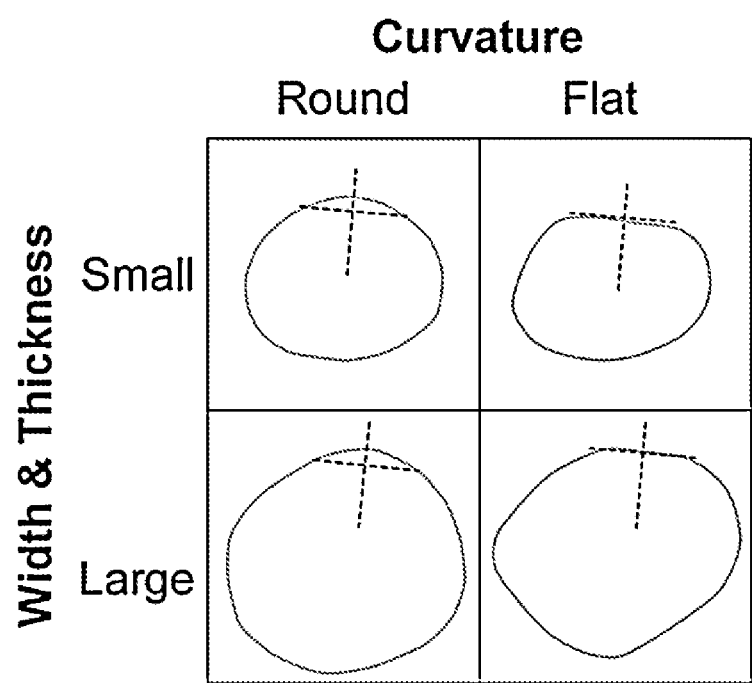
FIG. 4 shows various sizes and types of cross-sectional shapes of a human wrist in the area near a median nerve where the carpal device of the invention may be applied.

One key and unexpected finding from this study was a realization that changes in wrist profile between different individuals does not fit a conventional designation of small, medium, and large due to significant variations in wrist shapes in addition to a variation in wrist sizes. Analysis of the wrist shapes and sizes was conducted using MRI-obtained cross-sectional images of the wrist as seen in an exemplary view in FIG. 3. What can be noted is that the shape of the wrist is not generally oval as was broadly assumed previously. In fact, cross-sectional wrist profile varies significantly from one subject to the next. Importantly, the cross-sectional shape of the skin profile near the presumed location of the device (on the inner wrist above the median nerve, marked with dashed lines for a perpendicular and tangential directions) varies from generally flat to generally round, as seen in FIG. 4. This is noted in addition to the conventional notion of small and large wrists as corresponding to BMI.

Another important observation from the study is that in the area of intended application of the device—above the median nerve of the subject—there is only minimal difference in profile between large wrists and small wrists. This leads to a key difference between the approach for creating a desired curve of the device in the present invention and all curves and sizes of the prior art devices. The prior art generally teaches devices having the same side profile, which is then scaled up and down to cover small and large subjects. The present invention uses an unexpected discovery that the skin cross-sectional profile in the area above the median nerve varied predominantly by curvature, and not the overall size of the wrist or BMI of the subjects. Instead of providing small, medium and large devices of the same general profile, the present invention provides devices of varying curvature, which can be designated generally and flat, average and round.

Figures 5A, 5B:
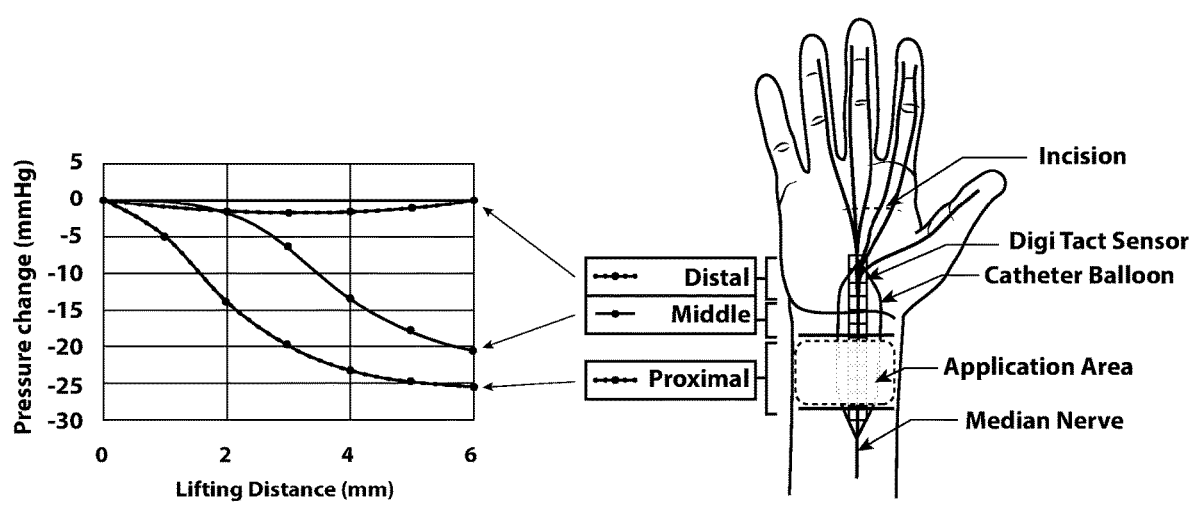
FIG. 5A shows a chart of changing pressure in the area of the wrist surrounding the median nerve as a function of changing lifting distance when the skin is moved away therefrom.
FIG. 5B shows an experimental set-up used to obtain the chart in FIG. 5A.

A further consideration for a proper profile design of a carpal tunnel syndrome relief device is the extent of pulling of the skin above the median nerve. As discussed above, there is a certain optimal extent of the pull, which is sufficiently effective but yet does not cause excessive skin compression in adjacent areas of the skin. To determine how the pressure change in the area of the median nerve depends on different distances of skin pull, a study was conducted of the median nerve of 10 fresh frozen cadavers ranging in weight from underweight to overweight. Pressure change as a function of skin lifting distance was evaluated. For each cadaveric hand, pressures within the wrist were measured using a linear array of tactile pressure transducers (DigiTacts tactile sensor by Pressure Profile Systems) inserted into the lumen of the carpal tunnel and under the median nerve. Along with the sensor, a PTA Balloon Dilation Catheter was inserted for standardization of the baseline pressure beneath the skin lifting carpal relief device—see FIG. 5B illustrating the experimental setup. The device was trimmed to its midportion and adhered to the skin and pulled up to 6 mm in 1 mm increments and then returned to its original position in 1 mm incremental steps pausing for 5 seconds at each displacement level by employing a robot to assure repeatability. The experimental procedure was repeated immediately for a total of 20 trials.

Results of the study are shown in FIG. 5A. The application of antebrachial tissue manipulation had a significant effect on pressure within the wrist. In general, as the magnitude of lifting distance increased, the tissue pressure decreased. A maximum decrease of 25 mmHg was observed at the 6 mm lifting distance compared to the baseline. For the wrist segment distal to the skin lifting device and proximal to the carpal tunnel, pressure at the 6 mm lifting distance was also significantly lower than baseline pressures.

In addition, paired comparisons of carpal tunnel pressure at 6 mm lifting distance revealed that there were significant differences between carpal tunnel pressures at trials 6-20 when compared to the first trial. The significant decrease in carpal tunnel pressure after the first 6 trials suggests that with repeated use, carpal tunnel pressure may be permanently reduced.

Results from this study showed that the pressure on the median nerve in a proximal portion of the wrist decreased as much as 25 mmHg with progressive lifting of overlying tissue up to 6 mm. However, if the skin lifting distance were reduced by just 2 mm, it would reduce the efficacy of the device by as much as 60%, as shown in FIG. 5A. This highlights the importance of personalized fit for the carpal tunnel syndrome relief to provide maximum efficacy. Too small of a gap between device curvature and skin curvature in cross-sectional view may reduce the efficacy of the device while too large of a gap may cause discomfort and possible tissue and skin irritation. In either case, patient compliance may be reduced.

Based on the above observation, the distance between the concave surface at the center of the device (corresponding to a peak of the middle portion curve on the concave side thereof) and the underlying skin in various embodiments of the device may be selected to be about 3 mm, about 3.5 mm, about 4 mm, about 4.5 mm, about 5 mm, about 5.5 mm, about 6 mm or any distance between about 3 mm and about 6 mm.

Because of a significant sensitivity of skin lifting distance on the extent of the pull, a close investigation of the skin curvature profile may be required as it is difficult to assess visually whether a certain device is a good fit for a particular subject or not. To achieve reliable results, objective skin profile scanning instruments may be required such as a 3-D scanner or an MRI imager for example. Other accessories contemplated for the purposes of assessing a space between a carpal tunnel syndrome relief device and the skin of the subject may include inserts of various sizes or a set of profiles of predetermined curvature allowing to measure the distance from the concave surface of the device at the peak of the middle portion and the underlying skin—prior to selection of the most suitable device and adhesive attachment of the skin to that device.

Based on the above considerations, to treat a subject suffering from a carpal tunnel syndrome, the present invention provides either a custom made single carpal tunnel syndrome relief device or a set of carpal tunnel syndrome relief devices, each having a predetermined curvature and size. An exemplary set of such devices are illustrated in FIGS. 6-8. FIG. 6 shows an exemplary ROUND device (top view—panel A, side view—panel B), FIG. 7 shows an exemplary AVERAGE device (top view—panel A, side view—panel B), and FIG. 8 shows an exemplary FLAT device (top view—panel A, side view—panel B).

As seen in FIG. 8 (and applicable to FIGS. 6 and 7), each carpal tunnel device 100 may generally comprise a resilient curved strip 110 of an elongated rectangular shape. The resilient strip 110 may be made to be generally symmetrical about a vertical axis drawn through the center thereof when viewed in cross-section side view with the center at the middle point defining a peak of the middle portion of the device. The middle portion 120 of the resilient strip 110 may be further configured for adhesive attachment of its concave side to the skin of the subject, while both peripheral portions 130 may be made adhesive-free.

In embodiments, an adhesive layer 180 may be permanently applied to the concave side of the middle portion 120 and may be protected by a removable protective liner 182. The adhesive choice needs to be carefully made. The adhesive needs to be very strong and should be a medical grade suitable for extended human contact. In embodiments, the adhesive may be selected from a silicone, acrylic or non-latex-based medical grade adhesives or alternatively selected from hydrocolloid medical grade adhesives designed to absorb fluids from the human skin.

The resilient strip 110 may be made from a number of polymer materials that provide enough rigidity and sufficient flexibility when in use. Exemplary polymers include PVC, PU, PP, PE, PET and ABS materials. It is preferred to select the material which is known to be hypoallergenic and is a medical grade.

In embodiments, the device 100 may include a plurality of perforation slots 108 allowing more of the skin area to be exposed to air through these perforations to breathe and allowing monitoring skin conditions while the device 100 is in use.

Figure 9A:
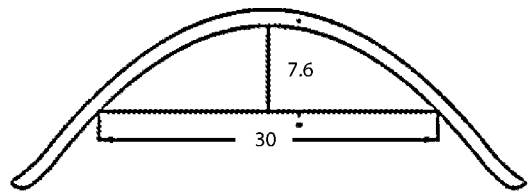
FIGS. 9 A, B, and C show cross-sections of a round device (FIG. 9A), average device (FIG. 9B) and flat device (FIG. 9C) together forming an exemplary set of carpal tunnel syndrome relief devices of the present invention.

The details of the predetermined curvature of the devices constituting the set of the present invention are shown in FIGS. 9A (round device), 9B (average device) and 9C (flat device). To distinguish between devices with various curves, the middle portion 120 of the device 100 curvature of said concave side is defined by a chord 122 with a predetermined length and a height 124 from a peak 126 of said middle portion 120 to said chord 122.

The length of the chord 122 may be selected to be about 20 mm, about 25 mm, about 30 mm, about 35 mm, or any other distance from about 20 mm to about 35 mm.

Figure 9B:
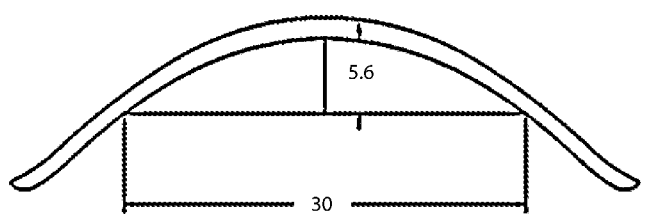
Figure 9C:
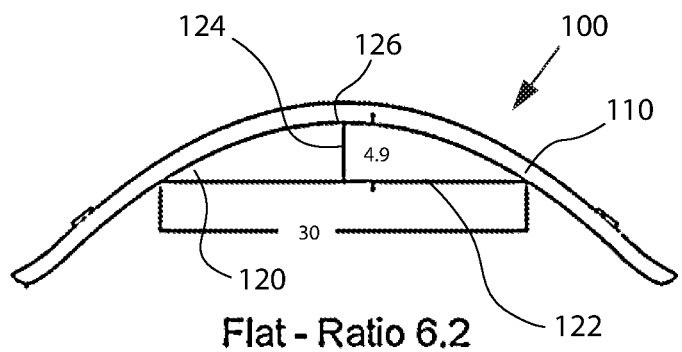

The height 124 may be selected to define a certain ratio of the chord length to the height which in turn defines a curvature of the middle portion 120. For a set of carpal tunnel syndrome relief devices, the height 124 may be selected in one example as follows:
  a first (round) carpal tunnel syndrome relief device with a ratio of the chord length to the height of about 3.5 to about 4.5—see an exemplary design in FIG. 9A with that ratio set at 3.9,
  a second (average) carpal tunnel syndrome relief device with the ratio of the chord length to the height of about 4.5 to about 5.5—see an exemplary design in FIG. 9B with that ratio set at 5.3, and
  a third (flat) carpal tunnel syndrome relief device with the ratio of the chord length to the height of about 5.5 to about 6.5—FIG. 9C shows an exemplary device with that ratio set at 6.2.

As can be easily appreciated by those skilled in the art, more than three devises may be provided in the set of the invention to assure an even closer fit of the device to the skin profile of a particular subject. However, given that only one of these devices will be eventually used, it may be not economically viable to increase the number of devices to more than 3. On the other side, providing only a single device or only two devices with different curvatures may not assure a good enough fit for all subjects and therefore the product of the invention may not be universally applicable.

Figure 10A:
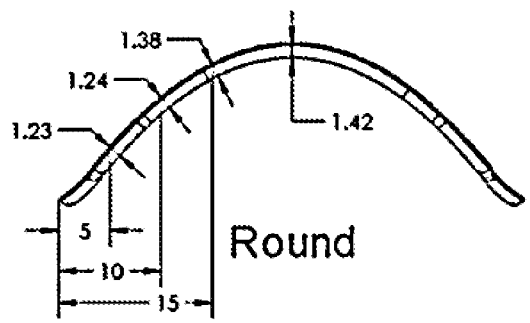
FIGS. 10 A, B, and C show a variety of thickness measurements throughout cross-sections of a round device (FIG. 10A), average device (FIG. 10B) and flat device (FIG. 10C) for an exemplary set of carpal tunnel syndrome relief devices of the present invention.
Figure 10B:
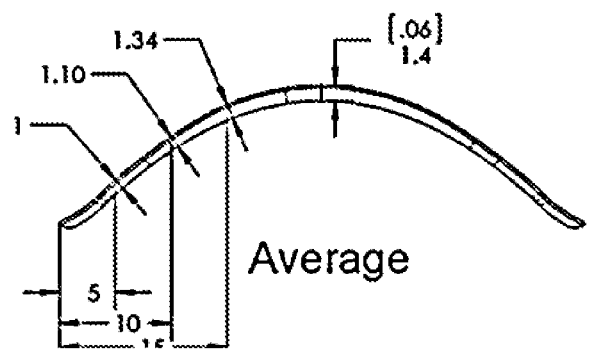
Figure 10C:
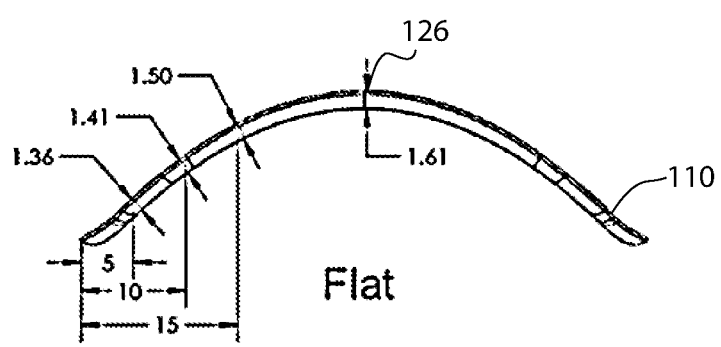

A further yet consideration for the design of the carpal tunnel syndrome relief device of the present invention is to balance the stiffness of the resilient strip with the ability to deform thereof. A too stiff strip may be difficult to apply while the strip which is too soft and pliable may not provide adequate skin pull. To address this design challenge, the resilient strip 110 of the present invention may be provided with varying thickness along its length when viewed from a side, as can be seen in FIGS. 10A (round device), 10B (average device), and 10C (flat device). Generally speaking, the thickness of the resilient strip may be selected to be between about 1 mm and about 1.8 mm. The maximum thickness of the resilient strip 110 may be located at the center 126 thereof. Away from the center 126, the thickness may be gradually reduced—symmetrically on both sides thereof at least in some embodiments of the present invention. This way, the periphery of the device 100 may be made to be more flexible and easier to deform than the middle portion thereof. This approach may allow for an easy application of the device while preserving the geometry of the middle portion profile which is needed to assure optimal extent of skin lifting.

In alternative embodiments, increased flexibility of the periphery as compared with the middle portion may be accomplished by varying the profile of the perforation slots 108. The width of the perforation slots 108 may be less in the middle portion and gradually increased towards the periphery, or alternatively more perforation slots may be provided in the periphery of the resilient strip 110 as compared with its middle portion (not shown in the drawings)

In embodiments, a method of obtaining a carpal tunnel syndrome relief may include the following steps:
 a. providing a set of carpal tunnel syndrome relief devices as described above,
 b. selecting one of these carpal tunnel syndrome relief devices using a predetermined criteria based on a curvature of said inner wrist of the subject, and
 c. resiliently deforming this selected carpal tunnel syndrome relief device and adhesively applying thereof to the skin area such that the concave side is less curved while being in contact with the skin area to provide continuous outward tension configured for lifting the skin area and underlying soft tissues. At the same time, the periphery of the resilient strip provides continuous skin compression at least some skin areas outside the skin area above said median nerve, whereby the carpal tunnel syndrome relief device is configured to shift the underlying soft tissues away from the median nerve and relieve compression of the median nerve.

During application of the selected carpal tunnel device 100 of the invention in step (c), it may be first placed orthogonally to the projected path of the median nerve (FIG. 1). The adhesive layer may be then exposed (by removing for example a protective masking liner 182) after which the device may be deformed to unfold the curvature of the median portion 110 and applied over the desired skin area. Once applied, the selected device 100 will cause the middle portion 110 to pull on the skin area and other local soft tissues up while the periphery of the device pushes down on the skin areas away from the location of the median nerve.

One example of a predetermined criteria for selecting one carpal tunnel syndrome relief device out of the set of such devices may be the distance from the peak of the middle portion 120 on a concave side thereof to the underlying skin. As discussed above, such distance may be selected to be between about 3 mm and about 6 mm. Each of the carpal tunnel syndrome relief devices of the set may be placed on the subject without removal of the adhesive masking liner 182 to assess the distance to the underlying skin. The best fit device may then be selected to assure such distance in the range described above. If two devices may be selected, a second predetermined criteria may be used, for example to select the device which provides that distance to the skin to be closest to about 5 mm.

Once the device 100 is applied, equilibrium of pressure and tension is found when the soft tissues are pulled up and away directly above the median nerve while soft tissues are pushed down in locations to the side of the median nerve. This equilibrium is maintained by a continuous pulling action provided by the device 100 causing a continuous shift in the position of the soft tissues relative to the median nerve leading to a continuous pressure relief thereof. Once the pressure is relieved on the median nerve, natural healing processes may take place. In embodiments, such healing process may also be enhanced with adjunct treatments or procedures, such as anti-inflammatory medications.

Device 100 of the present invention may be worn as needed, for example over the course of several weeks to a few months to provide continuous relief of pain and protect the area of the median nerve from occasional compression caused by manipulation of the arm of the subject. Avoidance of occasional rubbing of the nerve by surrounding tendons and ligaments may create favorable conditions for healing of the inflammation so that the pain does not come back when the device 100 is removed from skin.

In embodiments, a custom-made device may be provided instead of a set of devices having a predetermined shape. In this case, a 3-D scan of the skin profile of the subject may first be conducted. Once the skin profile is determined, a suitable shape of the device may be determined with a preselected distance between the peak of the middle portion 126 and the underlying skin to be at between about 3 mm and about 6 mm, such as for example about 5 mm. the resilient strip of a subject-specific profile may then be manufactured and provided to the subject.

3-D scanning of the wrist profile may be conducted using a 3-D scanner which may be a part of a smart phone. In one example, an iPhone face recognition camera may be used to scan a profile of the wrist. A dedicated phone app may be developed to support such scanning and to send appropriate data to a manufacturer of these devices. In other embodiments, such skin scanning software may also be used to select the best fit device from a set of such devices as provided by the manufacturer.

As an alternative to a 3-D scanning, various non-invasive imaging may be used such as MRI, ultrasound, CAT scan, or X-RAY imaging.

As the device is being used, skin moisture may be absorbed by the adhesive layer 180 and at some point, the device may be replaced. While the adhesive layer may be no longer useful, the resilient strip 110 may still be perfectly fine to be used further. To avoid replacing the entire device 100, in some embodiments of the invention, the adhesive layer 180 may be provided as a standalone separate component. In this case, initial and replacement applications of the device 100 may be conducted by changing just the adhesive layer 180 and keeping the resilient strip 110 the same throughout extended application of the device 100.

Figure 11A:
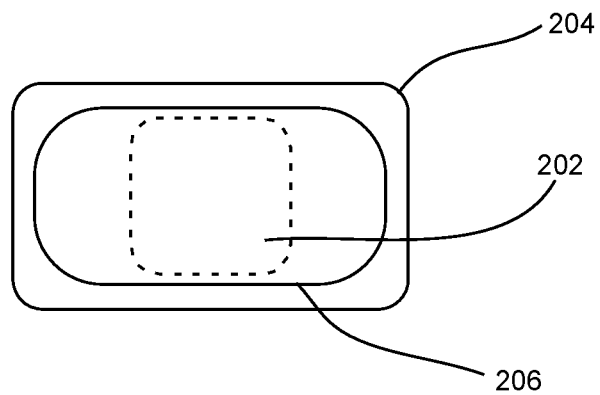
FIGS. 11A and 11B show a top view and side view of a stand-alone double-sided adhesive layer of the invention.
Figure 11B:
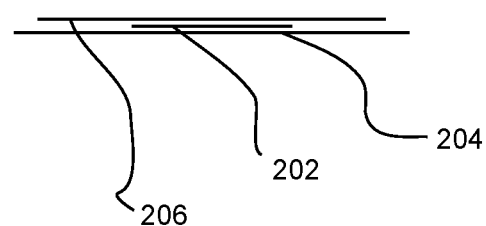

To achieve this result, the initial device configuration may include a combination of the resilient strip 110 packaged separately from the adhesive layer 180. As shown in FIGS. 11A (top view) and 11B (side view) a separate adhesive strip 200 may be provided to include a double-sided adhesive layer 202 surrounded on both sides thereof by a first protective liner 204 and the second protective liner 206. The size of the double-sided adhesive layer 202 may be selected to match the length of the middle portion 120 of the resilient strip 110. In embodiments, the first protective liner 204 may be made to be of a different size than the second protective liner 206 so as to ease the separation of the protective liners from the pressure sensitive adhesive layer 202.

While in some embodiments, the double-sided adhesive layer 202 may have the same adhesive on both sides, in other embodiments it may feature adhesives of different types and/or strengths, for example to assure a better adhesion to the resilient strip 110 as compared to the skin of the subject. In this case, removal of the resilient strip 110 may cause complete removal of the pressure sensitive adhesive layer 202 therewith, which may be preferred to facilitate a pain-free adhesive removal and replacement.

Figure 11C:
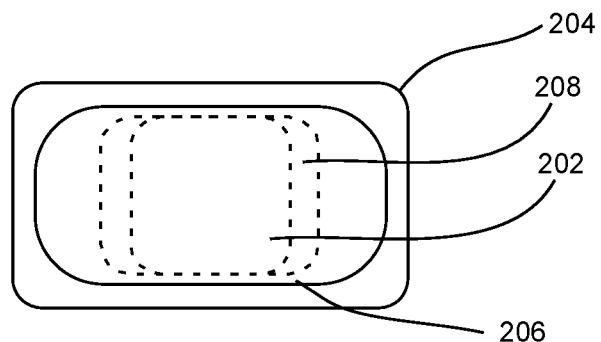
FIGS. 11C and 11D show a top view and a side view and a side view of a stand-alone adhesive strip with incorporated pull tab to remove adhesive after use.
Figure 11D:
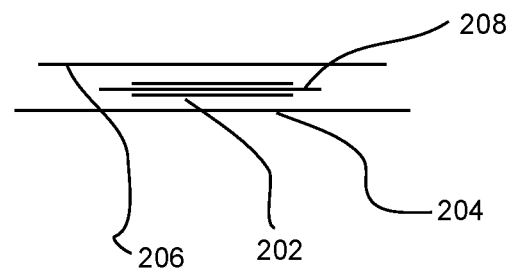

In further yet embodiments, a pull tab 208 may be embedded in the pressure sensitive adhesive layer 202 while protruding therefrom. Such pull tab 208 may be configured to not interfere or compromise the adhesive function on both sides of the adhesive layer 202—see FIGS. 11C and 11D—so as to facilitate removal of the pressure sensitive adhesive layer 202 from the skin and/or resilient strip 110 after use.

Figure 12:
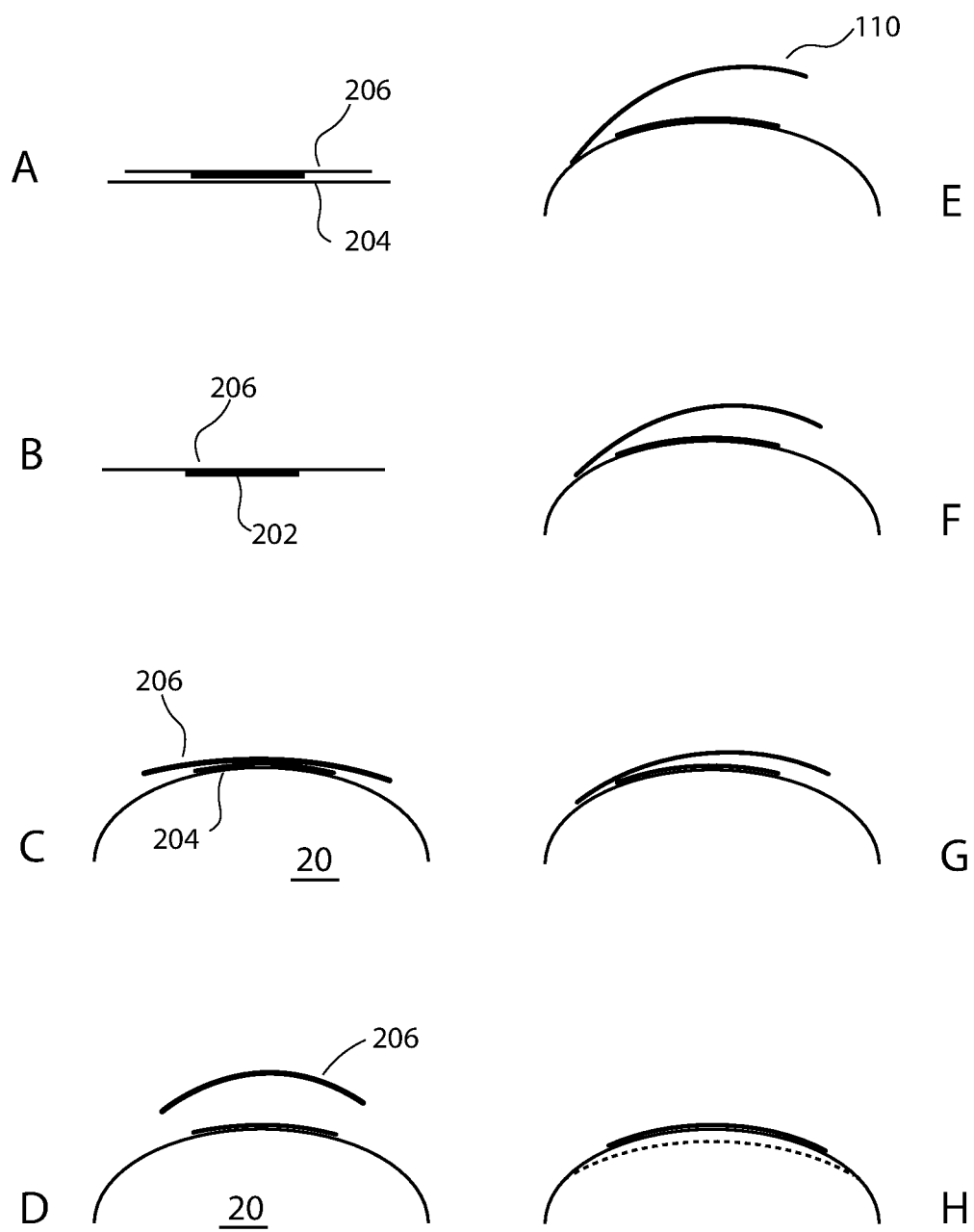
FIG. 12 shows various stages of deployment of the device using the double-sides adhesive layer shown in FIG. 11.

In use, the adhesive strip 200 may be selected to match the lengths of the adhesive layer 202 (FIG. 12, panel A) and the middle portion 120 of the resilient strip 110 (not shown). The first protective liner 204 may be removed and discarded (panel B) and the adhesive strip may be applied to the desired portion of the skin in a proximal portion of the wrist (panel B). The second protective liner 206 then may be removed (panel D) and the resilient strip 110 may then be deformed to assume lesser curvature and progressively applied to the skin so as to adhere to the skin at its respective middle portion (panels E, F, G). Release of the resilient strip 110 may then cause the lifting of the skin and underlying tissue (panel H).

Once the pressure sensitive adhesive layer 202 is saturated with moisture, soiled or becomes ineffective for some other reason, the resilient strip 110 may be removed and the adhesive layer 202 may be replaced using a fresh adhesive strip 200.

It is contemplated that any embodiment discussed in this specification can be implemented with respect to any method of the invention, and vice versa. It will be also understood that particular embodiments described herein are shown by way of illustration and not as limitations of the invention. The principal features of this invention can be employed in various embodiments without departing from the scope of the invention. Those skilled in the art will recognize or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12, 15, 20 or 25%.

All of the devices and/or methods disclosed and claimed herein can be made and executed without undue experimentation in light of the present disclosure. While the devices and methods of this invention have been described in terms of preferred embodiments, it will be apparent to those of skill in the art that variations may be applied to the devices and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method of obtaining relief for a carpal tunnel syndrome, said method comprising the following steps:
   a. providing a set of carpal tunnel syndrome relief devices, each carpal tunnel syndrome relief device configured for an adhesive application to a skin of a volar area on a proximal side of a wrist over a median nerve of a subject, each of said carpal tunnel syndrome relief devices comprising a resilient curved strip of a generally elongated rectangular shape with rounded edges, said resilient strip defining a middle portion equipped with or adapted to receive a pressure sensitive adhesive layer on a concave side thereof and an adhesive-free periphery, a curvature of said concave side is defined by a chord with a length of 20 mm to 35 mm and a height from a peak of said middle portion to said chord, said set comprising:
    a first carpal tunnel syndrome relief device with a ratio of said chord length to said height of 3.5 to 4.5,
    a second carpal tunnel syndrome relief device with the ratio of said chord length to said height of 4.5 to 5.5, and
    a third carpal tunnel syndrome relief device with the ratio of said chord length to said height of 5.5 to 6.5 b. evaluating a curvature of the volar area of the wrist of the subject and selecting one of said carpal tunnel syndrome relief devices to best achieve a distance between the peak of the middle portion of the selected device and underlying skin to be from 3 mm to 6 mm used as a predetermined criteria based on the a curvature of said volar area of the inner wrist of said subject, and c. resiliently deforming said selected carpal tunnel syndrome relief device during the application thereof to said skin of the volar area such that said concave side is less curved while being in contact with said skin area to provide continuous outward tension configured for lifting said skin of the volar area and underlying soft tissues, wherein said periphery provides continuous skin compression to at least some skin areas outside said skin area above said median nerve, whereby said carpal tunnel syndrome relief device is configured to shift said underlying soft tissues away from said median nerve and relieve compression of said median nerve without limiting wrist motion.

2. The method of obtaining relief for the carpal tunnel syndrome as in claim 1, wherein in case more than one carpal tunnel syndrome relief device from said set satisfy said predetermined criteria, a secondary predetermined criteria is used to select the carpal tunnel syndrome relief device with said distance between said peak of said middle portion and underlying skin to be closest to 5 mm.

3. The method of obtaining relief for carpal tunnel syndrome as in claim 1, comprising said set of carpal tunnel syndrome relief devices, wherein said pressure sensitive adhesive layer is located on said concave side thereof, said carpal tunnel device is further equipped with a removable protective liner covering said pressure sensitive adhesive layer.

4. The method of obtaining relief for carpal tunnel syndrome as in claim 1, comprising said set of carpal tunnel syndrome relief devices, wherein each of said carpal tunnel syndrome relief devices comprises a combination of said respective resilient strip and a stand-alone adhesive strip, said adhesive strip comprising a double-sided adhesive layer protected on both sides thereof by a first protective liner and a second protective liner.

5. The method of obtaining relief for carpal tunnel syndrome as in claim 4, comprising said set of carpal tunnel syndrome relief devices, wherein said double-sided adhesive layer is matched in size to said middle portion of said resilient strip.

6. The method of obtaining relief for carpal tunnel syndrome as in claim 4, comprising said set of carpal tunnel syndrome relief devices, wherein said double-sided adhesive layer incorporates a pull tab protruding therefrom and configured to ease removal of said adhesive layer from said device and from said skin area after use.

7. The method of obtaining relief for carpal tunnel syndrome as in claim 1, comprising said set of carpal tunnel syndrome relief devices, wherein said resilient strip has a maximum thickness at said peak of the middle portion, said thickness is gradually reduced away from said peak towards said adhesive-free periphery.

\* \* \* \* \*